United States Patent
Amouyel et al.

(10) Patent No.: US 6,790,618 B1
(45) Date of Patent: Sep. 14, 2004

(54) METHOD FOR DETERMINING THE SUSCEPTIBILITY OF A NIDDM PATENT TOWARD SULFONYLUREA THERAPY

(75) Inventors: Philippe Amouyel, Marco-En-Baroeul (FR); Nicole Helbecque, Marco-En-Baroeul (FR); Aline Meirhaeghe, Lille (FR)

(73) Assignees: Institut Pasteur de Lille, Lille (FR); Institut National de la Sante et de la Recherche Medicale (Inserm), Paris (FR)

( * ) Notice: Subject to any disclaimer, the term of this patent is extended or adjusted under 35 U.S.C. 154(b) by 0 days.

(21) Appl. No.: 09/913,731
(22) PCT Filed: Feb. 17, 2000
(86) PCT No.: PCT/EP00/01549
§ 371 (c)(1),
(2), (4) Date: Oct. 19, 2001
(87) PCT Pub. No.: WO00/49174
PCT Pub. Date: Aug. 24, 2000

(30) Foreign Application Priority Data

Feb. 19, 1999 (EP) .............................................. 99400410

(51) Int. Cl.⁷ ........................... C12Q 1/68; C12P 19/34; C07H 21/02; C07H 21/04
(52) U.S. Cl. ......................... 435/6; 435/91.2; 536/23.1; 536/23.5; 536/24.31; 536/24.33
(58) Field of Search .......................... 435/6, 91.1, 91.2; 536/23.1, 23.5, 24.31, 24.33

(56) References Cited

PUBLICATIONS

Hansen et al. Diabetes, vol. 47, Apr. 1998, pp. 508–606.*
Buck et al. Biotechniques 1999 27(3):528–536.*
Ahem, The Scientist, 1995, vol. 9, #15, pp. 1–5.*
Gibco BRL Catalog, 1993–1994, pp. R–67 and R–68.*
Gonzalez et al. Genbank Accession #L78223, Jun. 14, 1996.*
Hansen et al: "Decreased tolbutamide–stimulated insulin secretion in healty subjects with sequence variants in the high–affinity sulfonylurea receptor gene", *DIABETES*, vol. 47, No. 4, Apr. 1998, pp. 598–605.
Inoue et al: "Sequence variants in the sulfonylurea receptor (SUR) gene are associated with NIDDM in caucasians", *DIABETS*, vol. 45, Jun. 1996, pp. 825–831.

* cited by examiner

*Primary Examiner*—Jeffrey Fredman
*Assistant Examiner*—Sally Sakelaris
(74) *Attorney, Agent, or Firm*—Stites & Harbison PLLC; B. Aaron Schulman

(57) ABSTRACT

A method is provided for determining the susceptibility of a NIDDM patient towards sulfonylurea therapy by obtaining a sample from a NIDDM patient where the sample includes nucleic acid molecules containing a fragment of the SUR1 gene comprising the nucleotide in position −3 of exon 16 and detecting the presence or absence of the −3 t allele in position −3 of exon 6 whereby the presence of at least one −3 t allele identifies a NIDDM patient with a high susceptibility towards sulfonylurea therapy.

9 Claims, 1 Drawing Sheet

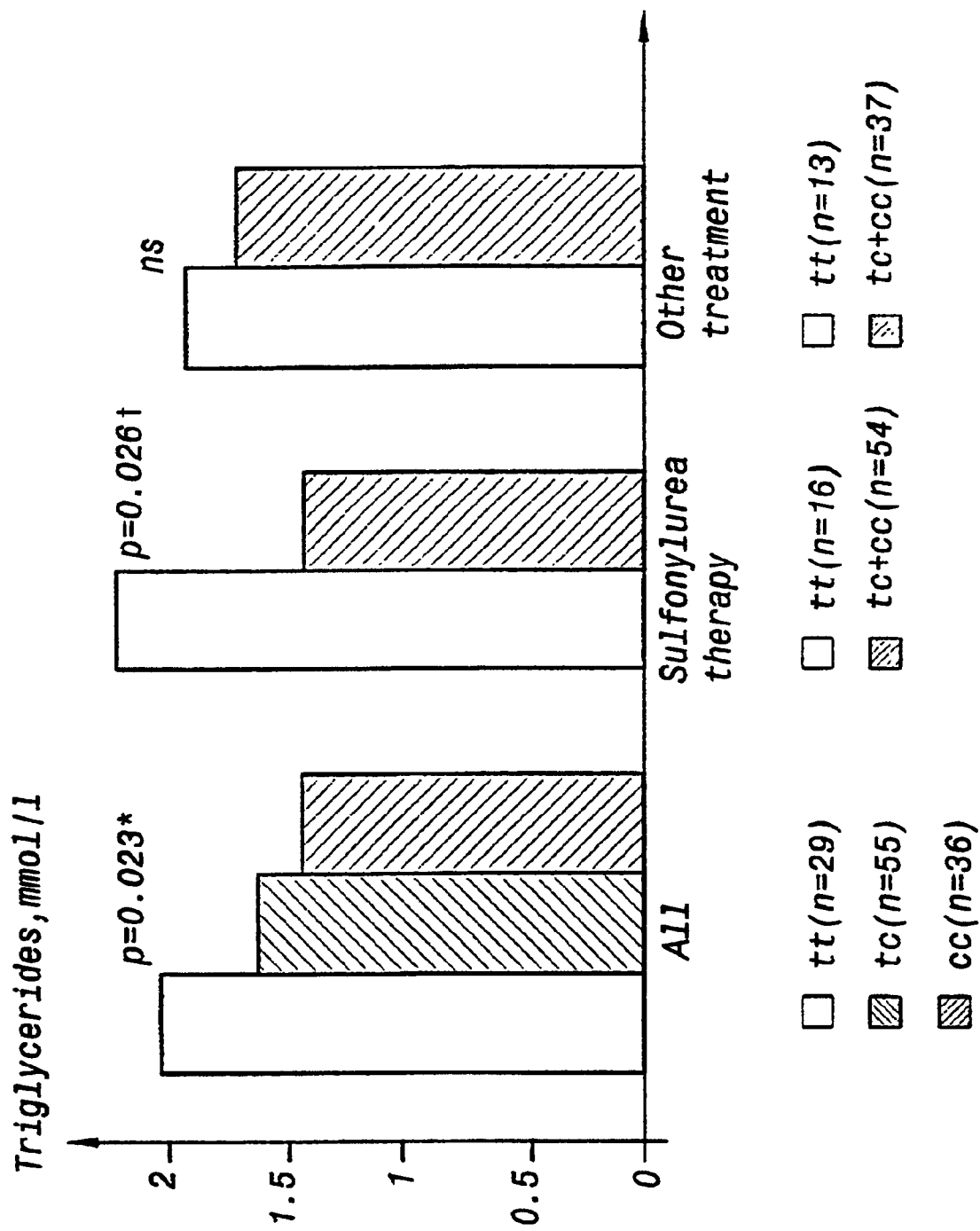

METHOD FOR DETERMINING THE SUSCEPTIBILITY OF A NIDDM PATENT TOWARD SULFONYLUREA THERAPY

FIELD OF THE INVENTION

The present invention relates to a method of determining the susceptibility of a non-insulin-dependent diabetes mellitus (NIDDM) patient toward a sulfonylurea therapy.

BACKGROUND OF THE INVENTION

Sulfonylureas are oral hypoglycaemic agents widely used in the treatment of NIDDM. They bind to the high affinity sulfonylurea receptor 1 (SUR1) and stimulate insulin release from pancreatic islet β cells. SUR1 is one of the protein that composes the ATP-sensitive potassium channel IKATP, closed by glucose metabolism in pancreatic β cells and triggering insulin exocytosis. The gene encoding SUR1 is located on chromosome 11p15.1. Mutations in the gene have been found in Familial Persistent Hyperinsulinemic Hypoglycaemia of Infancy (PHHI) (Thomas et al, (1995); Thomas et al (1986), Kane et al (1996) and Dunne et al (1997)) also known as Familial Hypersinsulinism (HI) (Nestorowicz et al (1996)). This disease is characterized by the elevation of serum insulin levels and severe hypoglycaemia.

Two case-control studies reported an association between genetic polymorphisms in the SUR1 gene and NIDDM. (Inoue et al, (1996) Hansen et al (1998)). To estimate the impact of the SUR1 genetic variability on NIDDM in population, the inventors characterized the genotypes of subjects for the most frequent polymorphism of the SUR1 gene, a $-3c \rightarrow t$ mutation located in intron 15, namely in position $-3$ of the exon 16 splice acceptor site (nucleotide 191 of SEQ ID n° 1) in a large representative sample of the French population aged 35 to 64 years.

As a result, they discovered that among the NIDDM patients, the frequency of the t allele was significantly lower in controls than in NIDDM patients.

In controls, no association was found between the polymorphism and body mass index, waist-to-hip ratio, fasting plasma glucose, fasting plasma insulin and lipid and lipoproteins profile. In NIDDM patients, the t allele was associated with a decrease in plasma triglycerides concentrations. NIDDM patients were stratified in two groups:subjects treated with sulfonylureas and subjects treated without. Decreases in plasma triglycerides and VLDL-cholesterol concentrations were found only in t allele bearers treated with sulfonylureas.

SUMMARY OF THE INVENTION

The present invention concerns the discovery that sulfonylurea therapy seems to be more efficient on hypertriglyceridemia reduction in NIDDM patients with the SUR1 intron 15 t allele than in NIDDM patients without, which may help to better target various therapies available in NIDDM treatment.

The present invention relates to a method for determining the susceptibility of a NIDDM patient toward sulfonylurea therapy comprising:

obtaining a sample from a NIDDM patient, said sample comprising nucleic acid molecules containing the fragment of the SUR1 gene comprising the nucleotide in position $-3$ of exon 16, detecting the presence or the absence of the $-3$ t allele in position $-3$ of exon 16, whereby the presence of at least one $-3$ t allele identifies a NIDDM patient with a higher susceptibility toward sulfonylurea therapy.

Sulfonylurea therapy in the sense of the instant invention identifies the current therapies of NIDDM utilizing oral hypoglycaemic agents binding the SUR1 receptor and stimulating insuline release from pancreatic islet β cells.

Such agents are derivatives of arylsulfonylurea having the following general formula:

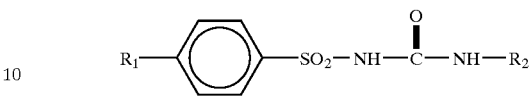

wherein $R_1$ may have the following meanings: Cl, $CH_3$,

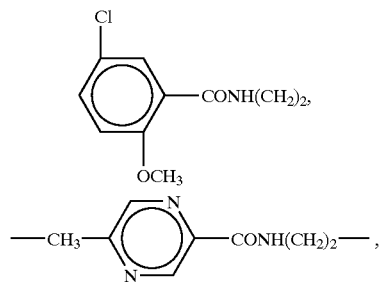

and $R_2$ may have the following meanings:
—$(CH_2)_2CH_3$
—$(CH_2)_3CH_3$

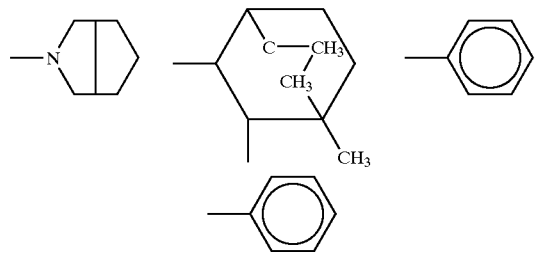

The main compounds are known under the following denominations: chlorpropamide, tolbutamide, gliclazide, glibomuride, glibenclamide, glipizide and buformine.

The sample from the patient may be any biological sample containing nucleic acids, namely a blood sample.

BRIEF DESCRIPTION OF THE DRAWING

FIG. 1 depicts triglycprides concentrations according to the experimental results of the present invention.

DETAILED DESCRIPTION OF THE PRESENT INVENTION

Intron 15 of the SUR1 gene is identified within the instant invention according to the nomenclature of Hansen et al (above) which teaching is hereby incorporated by reference.

The mutation responsible for the polymorphism referred to in the instant invention occurs on nucleotide $-3$ of the exon 16 splice acceptor site, the first nucleotide of the intron being numbered $-1$, the second $-2$ and the third $-3$ (SEQ ID n° 1, EMBL accession number L78223).

The detection of the $-3c \rightarrow t$ mutation in intron 15 may be performed by any known method in the art detecting DNA sequence variation.

A review of currently available methods of detecting DNA sequence variation can be found in a review by Grompe (1993).

In a preferred embodiment, the method comprises prior to step b) the step of amplifying said nucleic acid molecules using amplification primers that selectively anneal to and amplify a portion of said gene comprising the nucleotide in position −3 of exon 16.

One method for detecting the −3c→t mutation in the position −3 of exon 16 of the SUR1 gene comprises sequencing all or part of the sequence of intron 15 comprising said −3 nucleotide.

Direct DNA sequencing, either manual sequencing or automated fluorescent sequencing may be used.

Another approach is the single-stranded conformation polymorphism assay (SSCA') (Orita et al, 1989).

According to that approach, step b) comprises obtaining a first SUR1 gene fragment comprising the nucleotide in position −3 of exon 16 isolated from a human sample and a second SUR1 gene fragment comprising nucleotide −3c of exon 16, said second fragment corresponding to said first fragment, forming single-stranded DNA from said first SUR1 gene fragment and from said second SUR1 gene fragment, electrophoresing said single-stranded DNAs on a denaturating polyacrylamide gel, comparing the mobility of said single-stranded DNAs on said gel to determine if said single-stranded DNA from said first SUR1 gene fragment is shifted relative to said second SUR1 gene fragment.

The fragments which have shifted mobility on SSCA gels are then optionally sequenced to determine the exact nature of the DNA sequence variation.

Alternatively, instead of utilizing as the second gene fragment a gene fragment comprising nucleotide −3c of exon 16, one may utilize a second fragment comprising nucleotide −3 t of exon 16, whereby similar mobility is indicative of the presence of the −3c→3 t mutation in the position −3 of exon 16.

An other approach comprises contacting the nucleic acid molecules with a nucleic acid probe that selectively hybridizes to a portion of said 15 intron of SUR1 gene containing nucleotide −3 as shown in sequence SEQ ID n° 1 under hybridization conditions.

A further method comprises performing a restriction endonuclease digestion of said nucleic acid molecules thereby yielding a nucleic acid digest and contacting the digest with a nucleic acid probe that selectively hybridizes to a portion of said intron 15 of said SUR I gene containing nucleotide −3 as showed in sequence SEQ ID n° 1.

A still a further method comprises amplifying all or part of the SUR1 gene in said sample using a primer specific for allele −3 t and detecting the presence of an amplified product, whereby the presence of said product indicates the presence of said allele in the sample.

By "higher susceptibility", it is intented that not only hyperglycemia is decreased in NIDDM patients, but also hypertriglyceridemia, which is the main factor of cardiac risk for diabetic patients.

The instant invention also relates to a kit for determining the susceptibility of a NIDDM patient toward sulfonylurea therapy comprising a pair of nucleotide primers specific for amplifying all or part of the SUR1 gene comprising the nucleotide −3 of exon 16, and instructions relating to detecting the presence or a −3 t allele of exon 16 and correlating the presence of a −3t allele with a higher susceptibility toward sulfonylurea therapy.

In a preferred embodiment, the kit comprises a restriction enzyme that specifically cuts fragments comprising nucleotide −3 c/nucleotide −3 t, and reagents able to detect the presence of a cleaved fragment, the presence of a cleaved fragment being indicative of a higher susceptibility toward sulfonylurea therapy (−3 t)/ a lower susceptibility toward sulfonylurea therapy (−3 c).

The restriction enzyme is preferably Pst I that cleaves specifically fragments comprising the −3 t allele.

The present invention is described by reference to the following examples and the enclosed figure representing the effect of the SUR 1 exon 16 −3 c→t polymorphism on plasma triglycerides concentrations in NIDDM subjects, wherein * indicates that the β value was adjusted for age, gender, body mass index, alcohol and smoking consumptions (linear trend test) and † is indicative that the test used was the non-parametric Wilcoxon test.

Standard techniques well known in the art or the techniques specifically described below were utilized.

Population and Methods

Population Study

The population study was selected in 1995–1997 from three large representative French samples participating to the risk factor surveys of the WHO-MONICA (Multinational Monitoring of trends and determinants of Cardiovascular diseases) project (Ecological analysis of the association between mortality and major risk factors of cardiovascular disease. The World Health Organization MONICA Project. Int J. Epidemiol. 1994: 23:505–16 Tunstall-Pedoe H et al). This population study was randomly sampled from the electoral rolls of three geographical areas: the Urban Community of Lille (Lille) in the North, the department of Bas-Rhin (Strasbourg) in the East, the department of Haute-Garonne (Toulouse) in the South of France. The number of subjects recruited were 1195, 1131 and 1182 in Lille, Strasbourg and Toulouse areas respectively stratified on ten year age classes and gender. A fasting blood sample was drawn for all participants. In these samples, 123 NIDDM affected individuals were recovered on the basis of a medical diagnosis and on the existence of a specific treatment (Lille n=47, Strasbourg n=41, Toulouse n=35). A control group (n=1250) composed of individuals without diabetes, hypercholesterolemia or hypertension and without any treatment for these diseases was selected.

Biological Measurements

Glucose was measured by the glucose oxidase method (DuPont Dimension). Plasma insulin was measured by radio-immunoassay (Bilnsuline, ERIA Pasteur). Serum total cholesterol and triglyceride levels were measured by enzymatic methods (DuPont Dimension).

Genetic Analysis

Genomic DNA was extracted from white blood cells as described by Miller, A et al (1988). DNA amplification was performed using Polymerase Chain Reaction (PCR). Typing of the exon 16 −3 c→t polymorphism was achieved as described by Inoue et al (above).

Statistics

Statistical analyses were performed with the SAS statistical software, version 6.11 (SAS Institute Inc., Cary, N.C.). Genotype and allele distributions were compared with Pearson $\lambda^2$ statistical tests. The effect of the polymorphism on quantitative variables was tested with a multivariate analysis of covariance using a general linear model (proc GLM, type III SS). Interactions between genotypes and covariates were tested. Data for triglycerides, insulin, and glucose were log transformed to normalize the distributions. Statistical significance was considered at the $p<0.05$ level. When the number of subjects was low, genotypes were compared using non parametric Wilcoxon test.

Results

In control subjects, the frequency of the t allele of the SUR 1 exon 16 −3 c→t polymorphism was 0.45, 0.44 and 0.50 in Lille, Strasbourg and Toulouse studies respectively. When controls of the three studies were pooled, the frequency of the t allele was 0.46 while it was 0.53 in NIDDM patients. The adjusted relative risk for cc subjects to develop NIDDM was 1.76 (95 % Cl: [1.10–2.80], p=0.017) adjusted for age, gender, centre and body mass index.

Possible associations between the exon 16 −3 c→t polymorphism and clinical and biological variables such as body mass index (BMI), waist-to-hip ratio, plasma insulin, fasting-plasma glucose, or lipid variables in control and in NIDDM subjects were investigated. In controls, no association was found between the polymorphism and any variables listed above. In NIDDM patients, the −3 t allele was associated with decreased plasma triglycerides concentrations (2.03 [1.12–3.71] for tt, 1.62 [0.88–2.97] for tc and 1.45 [0.8–2.46] mmol/l for cc, p=0.023) and in an allele dose dependent manner (Table 2, FIG. 1).

As the sulfonylurea receptor 1 binds sulfonylurea agents, NIDDM patients were stratified In two groups: NIDDM patients receiving sulfonylureas (n=70) and patients receiving another treatment (n=52). Given the low number of cc homozygous subjects, tc and cc subjects were pooled to analyze a dominant effect of the −3 c allele. Wilcoxon tests were performed. In the group treated with sulfonylureas, the intron 16 −3 c allele was associated with a statistically significant decrease in plasma triglycerides concentrations (2.20 mmol/l [1.14–4.14] for tt versus 1.43 mmol/l [0.81–2.52] for tc+cc; p=0.026) whereas no association was found in the other group (FIG. 1).

The results indicate that the −3 t allele is associated with decreased plasma triglycerides concentrations in NIDDM patients, only in NIDDM patients receiving a sulfonylurea therapy, underlying a pharmacogenetic susceptibility to sulfonylurea treatment response.

This result is in accordance with previous works showing that oral sulfonylurea therapy, in addition to an improvement of glycemic control, decreases hepatic lipase levels and declines the production of triglycerides and VLDL-cholesterol in diabetics (Howard et al (1985); Taskinen et al (1986)). The results of the instant invention suggest that sulfonylurea therapy is more efficient on hypertriglyceridemia reduction in NIDDM patients bearing the SUR1 exon 16 −3 t allele underlying a pharmacogenetic susceptibility to sulfonylurea treatment response.

TABLE 1

Genotype and allele frequencies of the SUR 1 exon 16 −3c → t polymorphism in NIDDM patients and control subjects.

| | NIDDM patients | | | | |
| --- | --- | --- | --- | --- | --- |
| n | Lille 47 | Strasbourg 41 | Toulouse 34 | All 122 | Controls 1250 |
| Genotype | | | | | |

TABLE 1-continued

Genotype and allele frequencies of the SUR 1 exon 16 −3c → t polymorphism in NIDDM patients and control subjects.

| | NIDDM patients | | | | |
| --- | --- | --- | --- | --- | --- |
| n | Lille 47 | Strasbourg 41 | Toulouse 34 | All 122 | Controls 1250 |
| frequencies | | | | | |
| tt | 9 (0.19) | 11 (0.27) | 9 (0.27) | 29 (0.24) | 359 (0.29) |
| tc | 24 (0.51) | 18 (0.44) | 14 (0.41) | 56 (0.46) | 620 (0.50) |
| cc | 14 (0.30) | 12 (0.29) | 11 (0.32) | 37 (0.30)* | 271 (0.21) |
| allele frequencies | | | | | |
| t | 42 (0.45) | 40 (0.49) | 32 (0.47) | 114 (0.47) | 1338 (0.54) |
| c | 52 (0.55) | 42 (0.51) | 36 (0.53) | 130 (0.53)† | 1162 (0.46) |

Data are n (frequency %). Controls include Lille, Strasbourg, Toulouse studies.
All NIDDM subjects versus controls cc/tc + tt, p = 0.03.
†All NIDDM subjects versus controls c/t, p = 0.04.

Data are n(frequency %). Controls include Lille, Strasbourg, Toulouse studies.

All NIDDM subjects versus controls cc/tc+tt, p=0.03.

TABLE 2

Effect of the SUR 1 exon 16 −3c → t polymorphism in NIDDM subjects.

| Genotype intron 16 | tt | tc | cc | p |
| --- | --- | --- | --- | --- |
| n | 29 | 55 | 36 | |
| BMI, kg/m² | 30.7 ± 5.2 | 29.9 ± 6.2 | 30.1 ± 6.2 | ns |
| Insulin, μU/ml | 20.25 [11.73–34.95] | 17.64 [10.28–30.26] | 16.78 [8.50–33.11] | ns |
| Glucose, mmol/l | 8.25 [6.05–11.25] | 8.25 [6.05–11.25] | 8.67 [6.49–11.59] | ns |
| total cholesterol, mmol/l | 5.89 ± 0.94 | 5.69 ± 0.97 | 5.61 ± 1.28 | ns |
| Triglycerides, mmol/l | 2.03 [1.12–3.71] | 1.62 [0.88–2.97] | 1.45 [0.85–2.46] | 0.023* | p value was adjusted for age, gender, BMI, alcohol consumption and smoking consumptions (test for linear trend)

p value was adjusted for age, gender, BMI, alcohol consumption and smoking consumptions (text for linear trend)

What is claimed is:

1. A method for determining the susceptibility of a NIDDM patient toward sulfonylurea therapy comprising:
   a) obtaining a sample from a NIDDM patient, said sample comprising nucleic acid molecules containing the fragment of the SUR1 gene comprising the nucleotide in position −3 of exon 16,
   b) detecting the presence or the absence of the −3t allele of exon 16, whereby the presence of at least one −3t allele identifies a NIDDM patient with a higher susceptibility toward sufonylurea therapy relative to another NIDDM patient receiving a sufonylurea therapy without the at least one −3t allele.

2. The method according to claim 1, further comprising prior to step b) the step of amplifying said nucleic acid molecules using amplification primers that selectively anneal to and amplify a portion of said gene comprising the nucleotide in position −3 of exon 16.

3. The method according to claim 1, further comprising prior to step b) the step of amplifying said nucleic acid molecules using as amplification primers, the nucleic acid fragments of SEQ ID N° 2 and SEQ ID n° 3, that selectively anneal to and amplify a portion of said gene comprising the nucleotide in position −3 of exon 16.

4. The method of claim 1, wherein said detecting step b) comprises sequencing all or part of the sequence of intron 15 comprising said −3 nucleotide.

5. The method of claim 1, wherein said detecting step b) comprises contacting the nucleic acid molecules with a nucleic acid probe that selectively hybridizes to a portion of intron 15 of SUR1 gene containing nucleotide −3 as shown in SEQ ID n° 1 under hybridization conditions.

6. The method of claim 1, wherein the detecting step b) comprises performing a restriction endonuclease digestion of said nucleic acid molecules thereby yielding a nucleic acid digest and contacting the digest with a nucleic acid probe that selectively hybridizes to a portion of intron 15 of said SUR 1 gene containing nucleotide −3 as showed in SEQ ID n° 1.

7. The method of claim 1, wherein said detecting step b) comprises obtaining a first gene fragment comprising an initially unidentified nucleotide −3 of exon 16 isolated from the sample from the NIDDM patient and a second gene fragment comprising nucleotide −3c of exon 16, said second fragment corresponding to said first fragment but with a known −3c nucleotide, forming single-stranded DNA from said SUR1 gene fragment and from said second SUR1 gene fragment, electrophoresing said single-stranded DNAs on a denaturating polyacrylamide gel, comparing the mobility of said single-stranded DNAs on said gel to determine if said single-stranded DNA from said first SUR1 gene fragment is shifted relative to said second SUR1 gene fragment, and optionally sequencing said single-stranded DNA from said first SUR1 gene fragment having a shift in mobility.

8. The method of claim 1 wherein said detecting step b) comprises obtaining a first gene fragment comprising an initially unidentified nucleotide −3 of exon 16, isolated from the sample from the NIDDM patient and a second fragment comprising nucleotide −3t of exon 16, said second fragment corresponding to said first fragment but with a known −3t nucleotide, forming single-stranded DNA from said SUR1 gene fragment and from said second SUR1 gene fragment, electrophoresing said single-stranded DNAs on a denaturating polyacrylamide gel, comparing the mobility of said single-stranded DNAs on said gel to determine if said single-stranded DNA from said first SUR1 gene fragment has the same mobility as the said second SUR1 gene fragment, and optionally sequencing said single-stranded DNA from said first SUR1 gene fragment.

9. The method of claim 1 wherein said detecting step b) comprises amplifying all or part of a SUR1 gene in said sample using a primer specific for allele −3t and detecting the presence of an amplified product, whereby the presence of said product indicates the presence of said allele in the sample.

* * * * *

SEQUENCE LISTING

<160> NUMBER OF SEQ ID NOS: 3

<210> SEQ ID NO 1
<211> LENGTH: 253
<212> TYPE: DNA
<213> ORGANISM: Homo sapiens
<220> FEATURE:
<221> NAME/KEY: exon
<222> LOCATION: (194)..(226)
<223> OTHER INFORMATION: exon 17
<221> NAME/KEY: variation -continued

```
<222> LOCATION: (191)
<223> OTHER INFORMATION: corresponds to the intronic -3T/C change the
      present application refers to
<300> PUBLICATION INFORMATION:

<400> SEQUENCE: 1
atccaggtgc tgtgggaggg acagagattg agaagagtgc tttctgaccc cacagaggcc      60
atttggaaac cctgggaatt ggtgggaggg ttggaggttc cggattgctt ctcccctaag     120
actcagcgtg atggaaaggc aatggggtgg gaactaactg gtgttggtct gttcccattt     180
gtgttcccag cag cct tcc tga cag cga gat agg aga gga ccc cag           226 gtacagcctt gggactgggg tcagaag                                         253

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence:upstream
      primer

<400> SEQUENCE: 2
cccggcccca ctcacatctg                                                  20

<210> SEQ ID NO 3
<211> LENGTH: 22
<212> TYPE: DNA
<213> ORGANISM: Artificial Sequence
<220> FEATURE:
<223> OTHER INFORMATION: Description of Artificial Sequence: downstream
      primer

<400> SEQUENCE: 3
ggaggatggt taaaaggaga tt                                               22
```